United States Patent
Robinson

(10) Patent No.: US 10,493,693 B1
(45) Date of Patent: Dec. 3, 2019

(54) 3D-PRINTED APPARATUS FOR EFFICIENT FLUID-SOLID CONTACT

(71) Applicant: National Technology & Engineering Solutions of Sandia, LLC, Albuquerque, NM (US)

(72) Inventor: David Robinson, Hayward, CA (US)

(73) Assignee: National Technology & Engineering Solutions of Sandia, LLC, Albuquerque, NM (US)

(*) Notice: Subject to any disclaimer, the term of this patent is extended or adjusted under 35 U.S.C. 154(b) by 236 days.

(21) Appl. No.: 15/794,413

(22) Filed: Oct. 26, 2017

Related U.S. Application Data

(60) Provisional application No. 62/536,888, filed on Jul. 25, 2017.

(51) Int. Cl.
*B29C 64/153* (2017.01)
*F28D 15/04* (2006.01)
(Continued)

(52) U.S. Cl.
CPC .......... *B29C 64/153* (2017.08); *B29C 64/118* (2017.08); *B29C 64/268* (2017.08); *F28D 15/046* (2013.01)

(58) Field of Classification Search
CPC ... B29C 64/153; B29C 64/118; B29C 64/268; F28D 15/046; F28D 7/1607; F28D 7/1623; F28D 7/1638; F28D 7/1661; F28D 7/1676; F28D 7/1692; F28F 9/22; F28F 9/24; F28F 2009/222
(Continued)

(56) References Cited

U.S. PATENT DOCUMENTS

| | | | | |
|---|---|---|---|---|
| 4,044,825 A | * | 8/1977 | Gugenberger | F28F 7/02 165/165 |
| 5,061,660 A | * | 10/1991 | Park | C04B 35/652 252/516 |

(Continued)

OTHER PUBLICATIONS

Cabrera et al., "3D printing in chemical engineering and catalytic technology: structured catalysts, mixers and reactors", Royal Society of Chemistry 2017, 22 Pages.
(Continued)

*Primary Examiner* — Justin M Jonaitis
(74) *Attorney, Agent, or Firm* — Medley, Behrens & Lewis, LLC

(57) ABSTRACT

Additively manufactured monolithic structures for containing and directing flows of fluids are described herein, which can achieve high contact area between fluids and solids while maintaining uniform flow conditions and requiring low applied pressures to yield desired flow rates, for use in heat exchangers, chromatography columns, catalytic converters, etc. An exemplary monolithic structure comprises a plurality of tiled unit cells having a same shape, where the tiled unit cells are integrally formed as a single component. The tiled unit cells are arranged to define one or more interior regions of fluid flow, one or more inlets to each interior region of fluid flow, and one or more outlets to each interior region of fluid flow. The structures and methods of tiling herein are suited to additive manufacturing technologies such as projection stereolithography, multiphoton lithography, etc.

18 Claims, 11 Drawing Sheets

(51) Int. Cl.
*B29C 64/268* (2017.01)
*B29C 64/118* (2017.01)

(58) Field of Classification Search
USPC .............. 165/164, 159, 160, 165, 166, 167
See application file for complete search history.

(56) References Cited

U.S. PATENT DOCUMENTS

| | | | |
|---|---|---|---|
| 6,183,855 B1 * | 2/2001 | Buckley | B32B 5/18 |
| | | | 428/317.9 |
| 6,383,422 B1 * | 5/2002 | Hoffschmidt | B01D 39/2093 |
| | | | 210/510.1 |
| 6,592,787 B2 * | 7/2003 | Pickrell | C04B 38/0655 |
| | | | 264/44 |
| 6,609,043 B1 * | 8/2003 | Zoia | B29C 33/40 |
| | | | 700/119 |
| 7,574,830 B2 * | 8/2009 | Baker | E04B 1/19 |
| | | | 52/1 |
| 7,687,132 B1 * | 3/2010 | Gross | B22F 1/0007 |
| | | | 385/129 |
| 8,573,289 B1 | 11/2013 | Roper et al. | |
| 9,086,229 B1 * | 7/2015 | Roper | B29C 41/02 |
| 9,527,261 B1 | 12/2016 | Roper et al. | |
| 2004/0123980 A1 * | 7/2004 | Queheillalt | C23C 14/046 |
| | | | 165/133 |
| 2005/0202206 A1 * | 9/2005 | Wadley | E04C 2/3405 |
| | | | 428/116 |
| 2007/0102140 A1 * | 5/2007 | Tuma | H01L 23/3732 |
| | | | 165/80.3 |
| 2010/0300669 A1 * | 12/2010 | Jacobsen | F28F 13/003 |
| | | | 165/185 |
| 2014/0251585 A1 * | 9/2014 | Kusuda | F28D 1/06 |
| | | | 165/164 |

OTHER PUBLICATIONS

Fee, "3D-printed porous bed structures", Current Opinion in Chemical Engineering, vol. 18, 2017, pp. 10-15.
Femmer et al., "Estimation of the structure dependent performance of 3-D rapid prototyped membranes", Chemical Engineering Journal, vol. 273, 2015, pp. 438-445.
Billen, et al., "Understanding and Design of Existing and Future Chromatographic Support Formats", In Journal of Chromatography A, vol. 1168, 2007, pp. 73-99.
Couck, et al., "$CO_2$, $CH_4$ and $N_2$ Separation with a 3DFD-Printed ZSM-5 Monolith", In Chemical Engineering Journal, vol. 308, 2017, pp. 719-726.
Ferrizz, et al., "Monolithic Supports with Unique Geometries and Enhanced Mass Transfer", In Ind. Eng. Chem. Res., vol. 44, 2005, pp. 302-308.
Maloney, et al., "Multifunctional Heat Exchangers Derived from Three-Dimensional Micro-Lattice Structures", In International Journal of Heat and Mass Transfer, vol. 55, 2012, pp. 2486-2493.
Roper, et al., "Scalable 3D Biocontinuous Fluid Networks: Polymer Heat Exchangers Toward Artificial Organs", In Advanced Materials, vol. 27, 2015, pp. 2479-2484.
Su, et al., "Fully 3D-Printed Preconcentrator for Selective Extraction of Trace Elements in Seawater", In Analytical Chemistry, vol. 87, 2015, pp. 6945-6950.
Suleiman, et al., "Forced Convention Inside Metal Foam: Simulation Over a Long Domain and Analytical Validation", In International Journal of Thermal Sciences, vol. 86, 2014, pp. 104-114.
Witt, et al., "Microstructural Tunability of Co-Continuous Bijel-Derived Electrodes to Provide High Energy and Power Densities", In Journal of Materials Chemistry A, vol. 4, 2016, pp. 1000-1007.
Zhao, et al., "Combining a Distributed Flow Manifold and 3D Woven Metallic Lattices to Enhance Fluidic and Thermal Properties for Heat Transfer Applications", In International Journal of Heat and Mass Transfer, vol. 108, 2017, pp. 2169-2180.

* cited by examiner

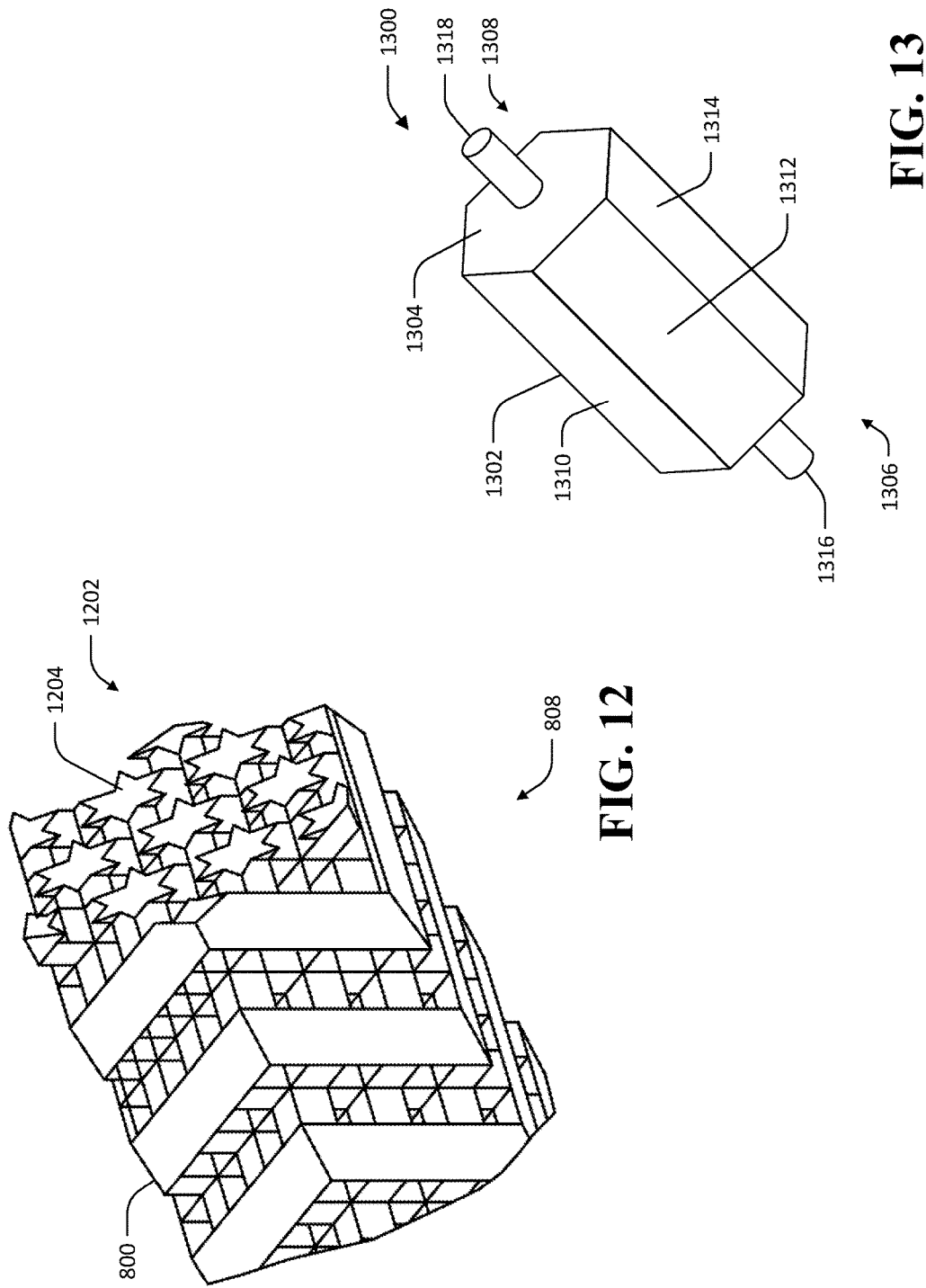

3D-PRINTED APPARATUS FOR EFFICIENT FLUID-SOLID CONTACT

RELATED APPLICATIONS

This application claims priority to U.S. Provisional Patent Application No. 62/536,888, filed on Jul. 25, 2017, and entitled "3D-PRINTED CHROMATOGRAPHY APPARATUS, SYSTEM AND METHODS", the entirety of which is incorporated herein by reference.

STATEMENT OF GOVERNMENTAL INTEREST

This invention was made with Government support under Contract No. DE-NA0003525 awarded by the United States Department of Energy/National Nuclear Security Administration. The U.S. Government has certain rights in the invention.

BACKGROUND

Heat exchangers and chromatography columns share several design objectives such as increased fluid-solid surface area, reduction of pressure drop requirements, and reduction of stagnant fluid flow. Chromatography is a technique for chemical separation of a fluid containing one or more chemical species. The fluid is transported through a structure where the fluid makes contact with an immobile phase such as a solid or a fluid-filled porous solid. Chemical species reversibly react with or are absorbed by the immobile phase to differing degrees, causing different chemical species to flow through the structure at different rates, thereby separating the species in the fluid.

Conventionally, chromatography has been conducted using packed-powder tubes containing powders that have reactive or sorbent features relative to one or more chemical species in an analyte fluid of interest. However, the need for high surface area for contact between the fluid and the packed powder in these conventional chromatography systems significantly impedes the flow of the fluid, requiring high pressures to maintain a desired flow rate. In heat exchangers, a thin, high-surface area solid is needed to separate two fluid phases, with similar flow considerations. Other applications with similar design considerations include catalyst columns, such as automotive catalytic converters; electrically resistive heaters; and filters, such as reverse osmosis filters for water desalination.

SUMMARY

The following is a brief summary of subject matter that is described in greater detail herein. This summary is not intended to be limiting as to the scope of the claims.

Various structures for containment and direction of a flowing fluid that are well-suited to construction by way of additive manufacturing methods are described herein. In one example, a structure described herein may be adapted for use as a chromatography column. In another example, a structure described herein may be adapted for use as a heat exchanger. Other uses for the structures described herein wherein a fluid is contained and directed through the structure are also contemplated.

In exemplary embodiments, a structure for containment and direction of a flowing fluid is formed by additive manufacturing. The structure is a monolithic structure comprising a plurality of tiled unit cells each having a same defined shape. The unit cells are arranged such that the structure defines an interior region through which a fluid flows. By way of example, the unit cells may be tiled so that fluid flows in a diagonal direction extending from a first corner of a unit cell in the tiling in a direction of a second corner of the unit cell. In other exemplary embodiments, the plurality of tiled unit cells are arranged such that the structure defines two separate interior regions. A first fluid flows in a first of the two separate interior regions, while a second fluid flows in a second of the two separate interior regions.

In various embodiments, a structure for containment and direction of a fluid may be formed by truncating a tiling of unit cells according to a desired shape of the structure. For example, a tiling of unit cells may be truncated along various planes to cause the structure to conform to boundaries of a container in which the structure is desirably housed. In still other exemplary embodiments, a structure for containment and direction of a fluid may be formed by successively tiling unit cells to form more complex structures.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

BRIEF DESCRIPTION OF THE DRAWINGS

FIG. 12 is a diagram of an exemplary embodiment of the tiling of FIG. 8.

FIG. 13 is a diagram of another exemplary containment structure for directing fluid into and out of a structure of tiled unit cells.

DETAILED DESCRIPTION

Figure 1:
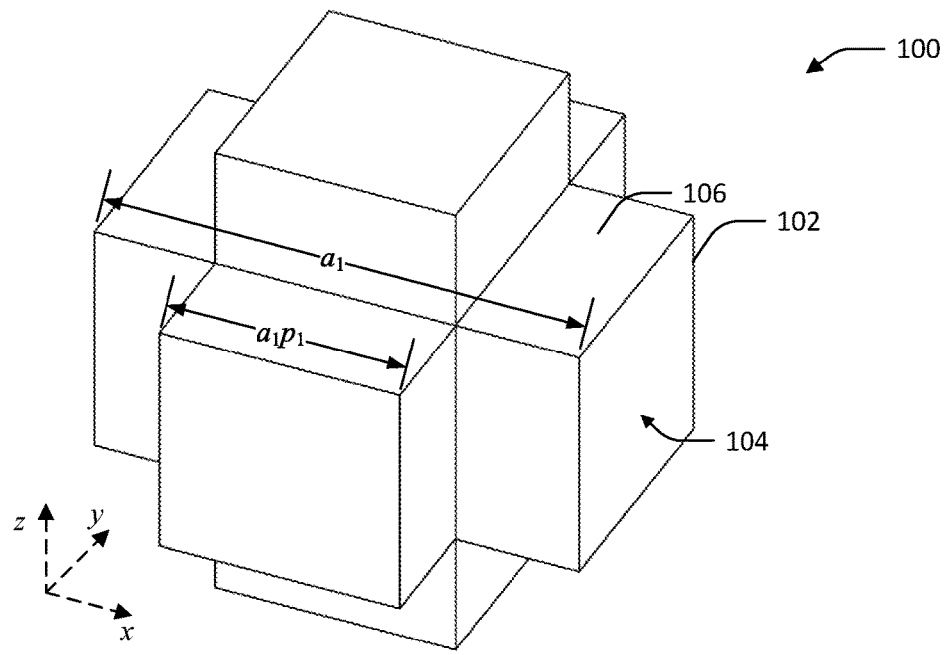
FIG. 1 is a diagram of an exemplary unit cell of a structure for directing flow of a fluid.

Various technologies pertaining to monolithic structures for directing and constraining flow of a fluid are now described with reference to the drawings, wherein like reference numerals are used to refer to like elements throughout. In some instances, for the sake of clarity of the drawings, where plural features are depicted the drawings, only a single exemplary instance of the feature may be labeled. The structures described herein are well-suited to manufacturing by additive manufacturing methods (3D printing). Furthermore, the structures described herein facilitate fluid flow with high surface area and low resistance to flow. Thus, structures described herein are suitable for applications such as chromatography, heat exchange, catalytic conversion, etc. In addition to providing structural support and flow confinement, the 3D-printed material may serve as the medium for energy or mass transport, or that induces chemical change, or it may be subsequently coated with such a medium.

In the following description, for purposes of explanation, numerous specific details are set forth in order to provide a thorough understanding of one or more aspects. It may be evident, however, that such aspect(s) may be practiced without these specific details. For example, while various specific structure geometries are described herein, it is to be understood that other structures are contemplated as being within the scope of the present disclosure. By way of example, while cubic unit cells and tilings of cubic unit cells are described herein, other geometries of unit cells are contemplated (e.g., hexagonal prism unit cells, logpile unit cell, etc.) in connection with the structures described herein.

In other instances, well-known structures and devices are shown in block diagram form in order to facilitate describing one or more aspects. Further, it is to be understood that functionality that is described as being carried out by certain system components may be performed by multiple components. Similarly, for instance, a component may be configured to perform functionality that is described as being carried out by multiple components.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form. Additionally, as used herein, the term "exemplary" is intended to mean serving as an illustration or example of something, and is not intended to indicate a preference.

It is to be understood that any of the structures described herein may be manufactured according to additive manufacturing methods, wherein an integral monolithic structure is formed through successive addition of material to the structure. Where a structure is described herein as being formed in a succession of steps (e.g., defining a unit cell, tiling a unit cell, truncating one or more faces of a structure, etc.) it is to be understood that the succession of steps may be conceptual rather than physically implemented steps. For example, where a structure is described as being formed by tiling a unit cell, it is to be understood that the tiling may be accomplished by defining the tiled structure in a computer-aided design (CAD) or other file usable by an additive manufacturing system.

Figure 2:
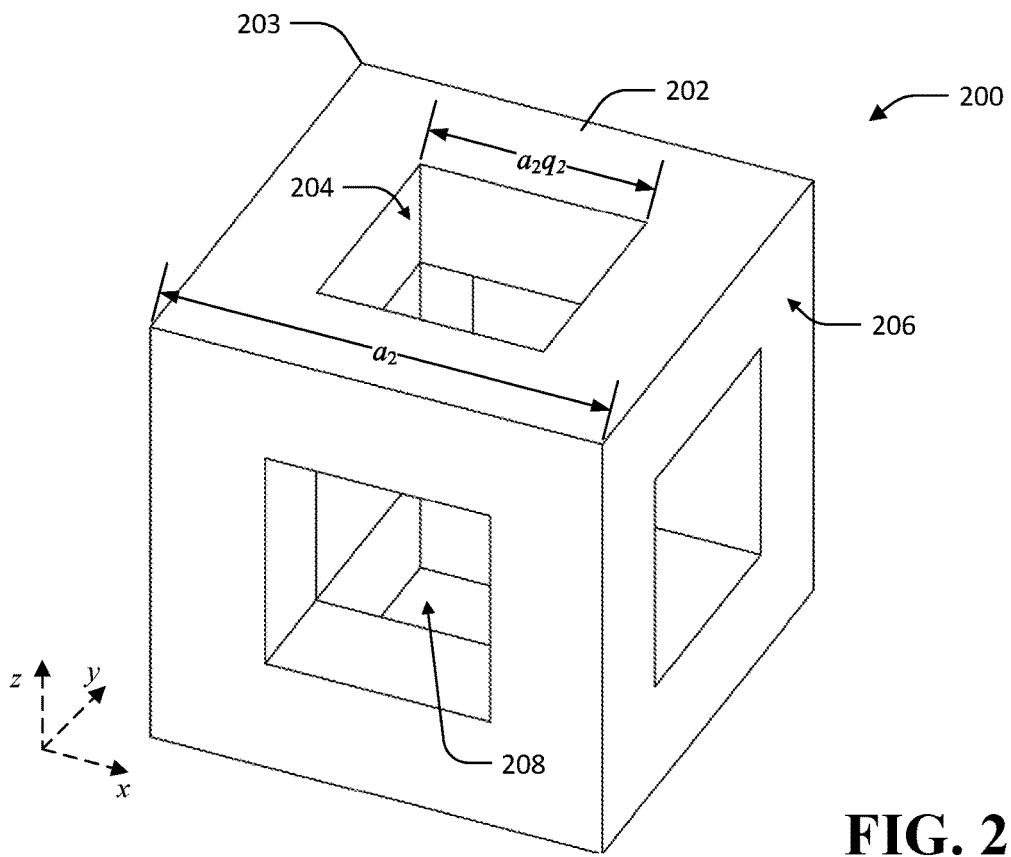
FIG. 2 is a diagram of another exemplary unit cell of a structure for directing flow of a fluid.

With reference to FIGS. 1 and 2, exemplary unit cells that facilitate construction of additively manufactured structures for directing and containing a flow of a fluid are illustrated. Referring now solely to FIG. 1, a 3D cross unit cell 100 is shown. The 3D cross unit cell 100 comprises a cubic shape that has six protruding struts 102 extending outward from faces of a central cube. Each of the protruding struts 102 extends outward at 90° angles from each of four adjacent struts 102 of the 3D cross unit cell 100. The 3D cross unit cell 100 has six faces 104, one for each of the struts 102. Each of the struts 102 further defines four sides 106 extending outward from a face of the central cube.

A fluid volume fraction for the unit cell 100, $$\frac{V_f}{a_1^3},$$

assuming the fluid fills the entire unoccupied space of a cube of length $a_1$ (not shown) that encloses the cell 100 and has volume $a_1^3$, is given by the following equation:

$$\frac{V_f}{a_1^3} = 1 - p_1^3 - \frac{6}{2}(1 - p_1)p_1^2 \qquad (1)$$

where $a_1 p_1$ is the edge length of the square faces 104 of the 3D cross 100 and $a_1$ is a distance between opposite faces of the 3D cross 100. Thus, in a tiling of the unit cell 100, fluid is contained in spaces between unit cells 100 such that fluid may be considered to surround the sides 106 of the struts 102 of the unit cells 100.

A surface area, A, of the boundary between the fluid and the structure of the unit cell 100 is given by $$\frac{A}{a_1^2} = \frac{24}{2}(1 - p_1)p_1 \qquad (2)$$

Referring now solely to FIG. 2, a cubic-edge unit cell 200 is shown. The cubic-edge unit cell 200 comprises solid struts 202 extending along each edge of a cube shape. Each of the struts 202 intersects two other struts at right angles to form corners 203 of the cubic-edge unit cell 200. In exemplary embodiments, the struts 202 may have rounded or chamfered cross sections. In other exemplary embodiments, intersection points of struts may be rounded or chamfered. The cubic-edge unit cell 200 comprises six square openings 204, wherein each of the square openings 204 extends through a respective face 206 of the cubic unit cell 200. The cubic unit cell 200 further comprises a hollow interior portion 208 that is contained within the faces 206. The openings 204 extend through the faces 206 such that a fluid flowing through one of the openings 204 may freely flow through the hollow interior portion 208 to any other of the openings 204.

A fluid volume fraction, $$\frac{V_f}{a_2^3},$$

assuming the fluid fills the entire unoccupied space of a cube of length $a_2$ (not shown) that encloses the cell 200 and has volume $a_2^3$, is given by the following equation:

$$\frac{V_f}{a_2^3} = q_2^3 + \frac{6}{2}(1-q_2)q_2^2 \quad (3)$$

where $a_2 q_2$ is the edge length of the square holes 204 in the faces 206 of the cell 200, and $a_2$ is the edge length of the struts 202 of the cell 200. In a tiling of the unit cell 200, fluid is contained within an interior region defined by the hollow portion 208 and the holes 204 of the unit cells 200. Similarly to the 3D cross unit cell 100, the surface area, A, of the boundary between the fluid and the structure of the unit cell 200 is given by:

$$\frac{A}{a_2^2} = \frac{24}{2}(1-q_2)q_2 \quad (4)$$

The unit cells 100 and 200 are complements in that when the unit cell edge lengths $a_1$ and $a_2$ are the same, and the fluid volume fractions $$\frac{V_f}{a_1^3}$$

and $$\frac{V_f}{a_2^3}$$

as defined above are equal to ½, the cells 100 and 200 are spatial inverses of each other. Thus, under these conditions, the 3D cross unit cell 100 fits inside the hollow space 208 defined by the struts 202 and the openings 204 of the cubic-edge unit cell 200. Put another way, the cubic-edge unit cell 200 fits around the struts 102 of the 3D cross unit cell 100. For either the 3D cross unit cell 100 or the cubic-edge unit cell 200, the solid volume fraction $V_s$ may be defined as: $V_s = a^3 - V_f$ where a is either $a_1$ or $a_2$, as appropriate.

Figure 3:
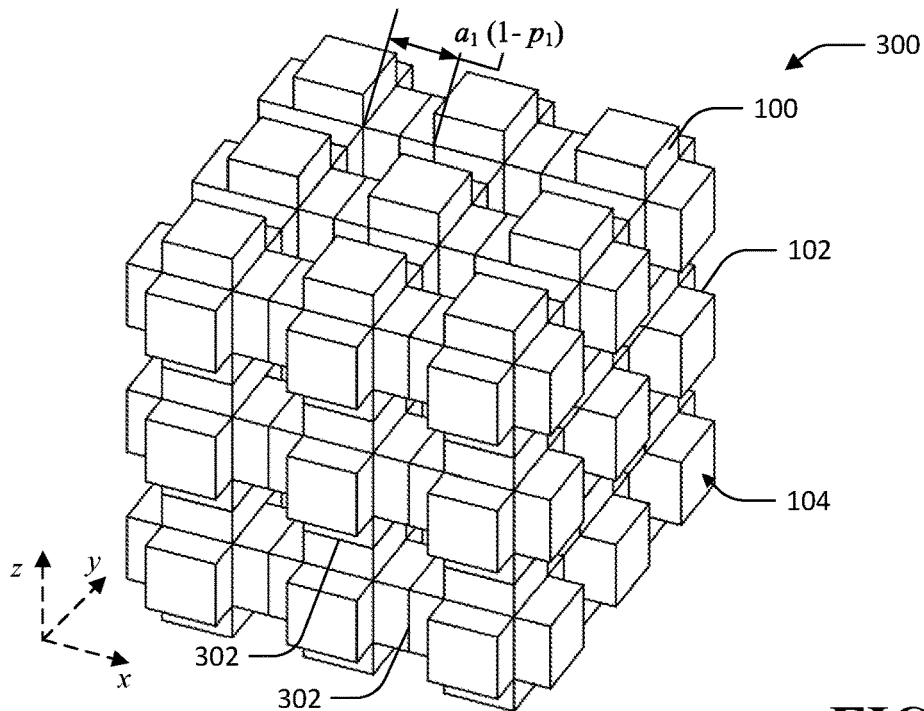
FIG. 3 is a diagram of an exemplary tiling of the unit cell of FIG. 1 to define a structure for directing flow of a fluid.
Figure 4:
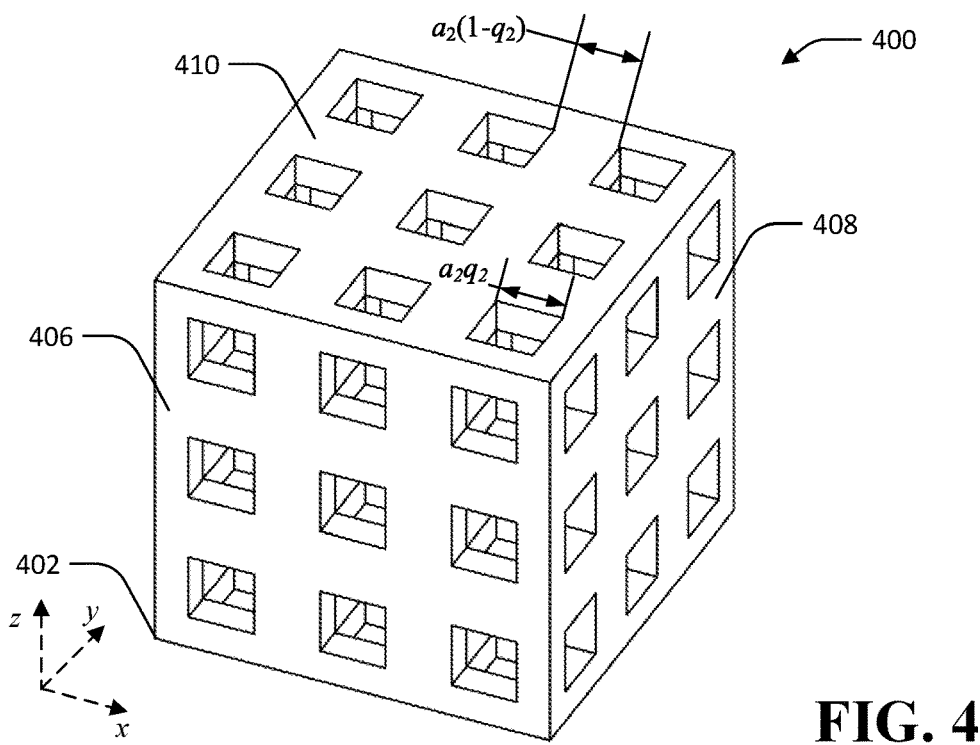
FIG. 4 is a diagram of an exemplary tiling of the unit cell of FIG. 2 to define a structure for directing flow of a fluid.

Referring now to FIGS. 3-4, exemplary tilings 300, 400 of the unit cells 100, 200, respectively are illustrated. The exemplary tilings 300, 400 are monolithic structures that are integrally formed as a single component rather than being constructed from a plurality of discrete components. For example, the tilings 300, 400 may be constructed by way of additive manufacturing techniques that build monolithic structures layer by layer. The exemplary tilings 300, 400 are suited to containment and direction of a single fluid within a contiguous region bounded by the solid structure of the tilings 300, 400. Thus, the tilings 300, 400 respectively define a first region in which a fluid flows through the tilings 300, 400 and a second region occupied by the solid portions of the unit cells 100, 200, where the first and second regions occupy the entire volume of the tilings 300, 400. The tilings 300, 400 are suitable for applications such as chromatography, catalytic conversion, etc., wherein a fluid makes contact with a solid phase of material to perform some function or facilitate a chemical or other reaction.

Referring solely now to FIG. 3, the exemplary tiling 300 includes a plurality of the 3D cross unit cells 100. The exemplary tiling 300 is a 3×3×3 tiling of 3D cross unit cells 100 wherein the unit cells 100 are tiled in x, y, and z directions extending in the direction of respective faces 104 of the unit cells 100, such that adjacent unit cells 100 in the tiling 300 meet at faces 104 of their respective struts 102. While boundaries 302 between unit cells 100 are shown in the exemplary tiling 300 depicted in FIG. 3 for purposes of illustrating arrangement of the unit cells 100, it is to be understood that such boundaries 302 may not be present in an additively manufactured embodiment of the exemplary tiling 300. For example, in an additively manufactured embodiment of the exemplary tiling 300, the struts 102 of the unit cells 100 extend seamlessly into one another such that a boundary between unit cells is not readily determinable. In the exemplary tiling 300, a distance between neighboring struts 102 of the unit cells 100 is given by $a_1(1-p_1)$.

Referring solely now to FIG. 4, the exemplary tiling 400 is a 3×3×3 tiling of the exemplary unit cells 200. As in the exemplary tiling 300, to form the tiling 400 of the unit cells 200, the unit cells 200 are tiled in x, y, and z directions extending from a corner 402 of a first unit cell 404 in the unit cells forming the tiling 400, the boundaries of which unit cell 404 are not shown. The tiling 400 is a cubic shape comprising six faces (e.g., faces 406-410) in which are disposed square openings 412 having edge length $a_2 q_2$. A distance between the openings 412 is given by $a_2(1-q_2)$. The openings 412 access an interior region through which fluid is able to flow into and out of the structure 400.

With respect to the tilings 300, 400, while the fluid volume $V_f$ for each tiling can be expressed as a unitless volume fraction (fluid volume per unit cell volume $$\frac{V_f}{a_1^3}$$

or $$\frac{V_f}{a_2^3}),$$

surface area between the fluid phase and the solid phase per unit cell volume is defined with units of reciprocal distance as follows:

$$\frac{A}{a_1^3} = \frac{24}{2a_1}(1-p_1)p_1 \quad (5)$$

with respect to the unit cells 100 of tiling 300, and:

$$\frac{A}{a_2^3} = \frac{24}{2a_2}(1-q_2)q_2 \quad (6)$$

with respect to the unit cells 200 of tiling 400. Therefore, as the unit cell edge length $a_1$ or $a_2$ increases, the surface area between the fluid and solid phases increases in proportion to the square of the length. Thus, if smaller unit cells are tiled in a given tiling volume, the surface area between the fluid phase and the solid phase of a given unit cell decreases, but the surface area in the tiling volume increases, because the number of unit cells in the tiling volume increases in proportion to the cube of the unit cell edge length.

Figure 5:
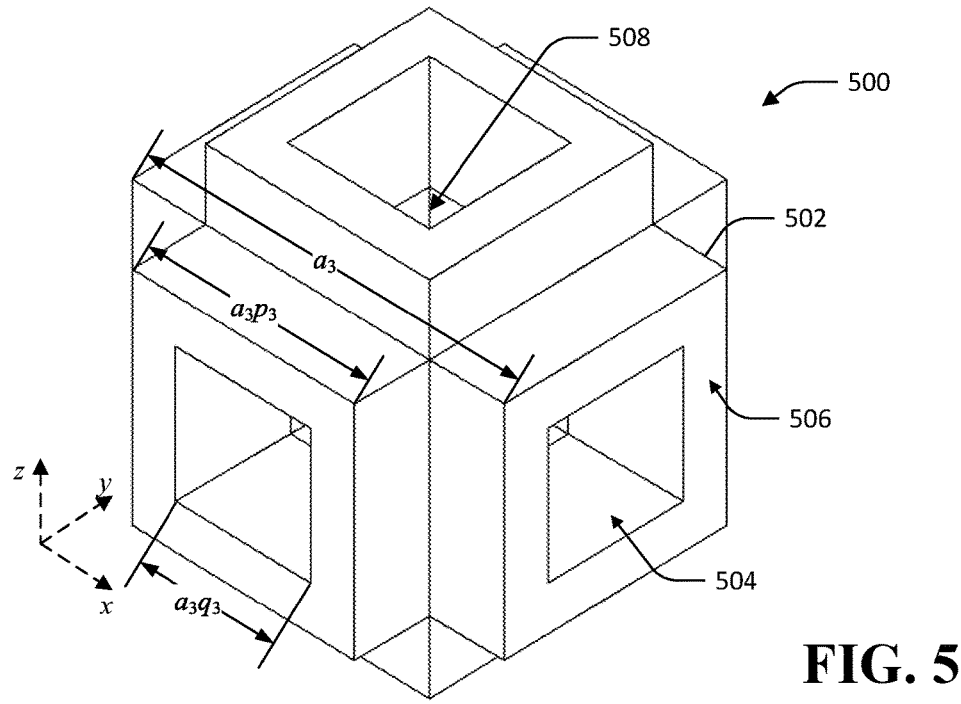
FIG. 5 is a diagram of an exemplary unit cell of a structure for directing separate flows of two different fluids.

Referring now to FIG. 5, another exemplary unit cell 500 is depicted that is suitable for constructing a structure for separately directing and containing the flow of two fluids simultaneously. Accordingly, the unit cell 500 is suited to applications such as heat exchange, and applications where selective transport of mass or energy from one fluid phase to another is desirable, such as separators for flow batteries, reverse osmosis membranes for water desalination, etc. The unit cell 500 is a bicontinuous cubic unit cell comprising a hollow 3D cross. The unit cell 500 has features similar to features of the 3D cross unit cell 100 and the cubic-edge unit cell 200. The unit cell 500 has the shape of a cube with six square struts 502 extending from the faces of the cube. The unit cell 500 further comprises square openings 504 disposed in faces 506 of each of the struts 502. As in the unit cell 200, the openings 504 extend through the struts 502 to a hollow interior region 508 of the cell 500. Hence, a fluid flowing through a first one of the openings 504 can flow through the interior region 508 of the cell 500 to any of the other openings 504. The square struts 502 have an edge length of $a_3 p_3$, while the square openings 504 in the faces 506 of the struts 502 have an edge length of $a_3 q_3$, by which definition $p_3 > q_3$. A distance between opposite faces 506 of the cell 500 is depicted in FIG. 5 as $a_3$.

Figure 6:
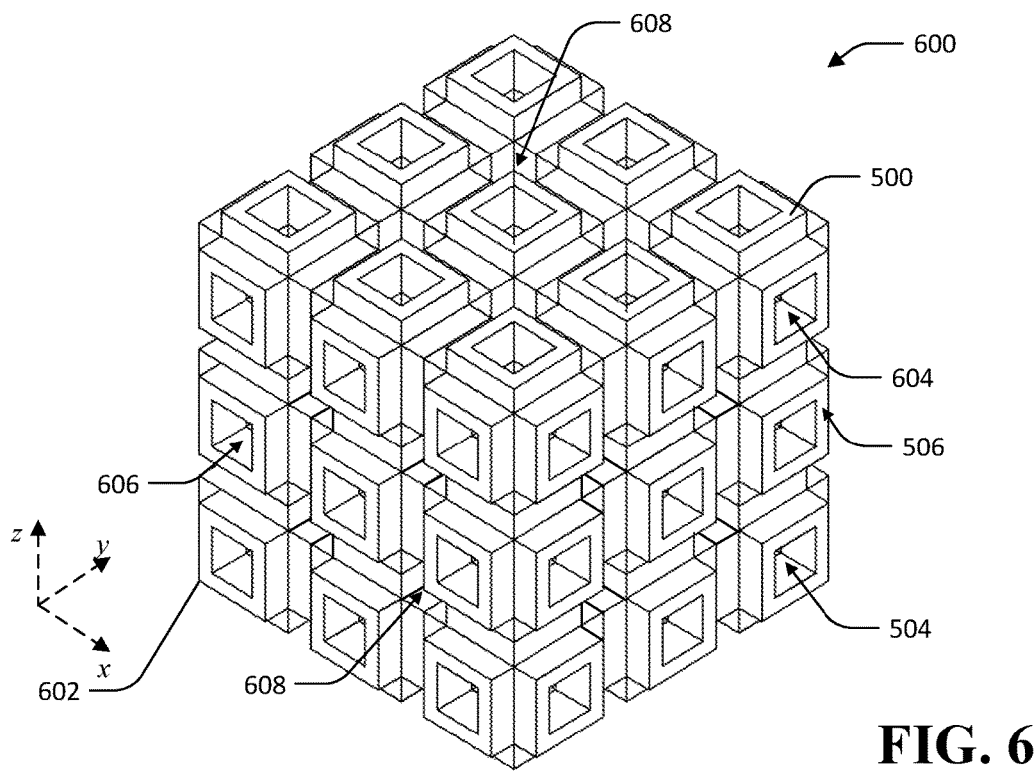
FIG. 6 is a diagram of an exemplary tiling of the unit cell of FIG. 5 to define a structure for directing separate flows of two different fluids.

Referring now to FIG. 6, an exemplary tiling 600 of the unit cell 500 is illustrated, wherein the tiling 600 defines a first interior region in which a first fluid can flow and a second interior region separate from the first interior region, wherein a second fluid flows in the second interior region. The tiling 600 is a 3×3×3 tiling of the unit cells 500 in the x, y, and z directions as extending from a corner of a first unit cell 602 in the unit cells making up the tiling 600. The unit cells 500 in the tiling 600 are arranged such that the unit cells 500 interface along their faces 506. The first interior region in which the first fluid flows is accessed by way of the square openings 504 in the faces 506 of the unit cells 500. The first interior region extends through the structure 600 such that fluid flowing through a first opening 604 in the structure 600 may flow out of any other of the openings 504 of the unit cells 500 of the structure 600 (e.g., opening 606). The second interior region in which the second fluid flows is accessed by voids 608 formed by the tiling of the unit cells 500 along their faces 506. The second interior region, like the first, extends through the structure 600 such that fluid flowing into the second interior region of the structure 600 by way of a first void in the voids 608 may flow out of the second interior region of the structure 600 by way of any of the voids 608.

From the foregoing it is to be understood that the tiling 600 provides a structure that can contain, direct, and keep separate two fluid flows. A first fluid flows through the structure by way of the openings 504 in the faces 506 of the cells 500, while the second fluid flows through the structure by way of the voids 608 formed between cells 500 by the tiling of the cells 500 along their faces 506. In the tiling 600, the two fluid phases are separated by the material making up the cells 500. The thickness of the material separating the phases is given by $(p_3 - q_3) a_3 / 2$. For a given cube (not shown) of length $a_3$ enclosing a unit cell 500 in the tiling 600, the volume of the first fluid phase, $V_{f1}$, the volume of the second fluid phase, $V_{f2}$, and the volume of the solid phase, $V_s$, are given by:

$$\frac{V_{f1}}{a_3^3} = q_3^3 + \frac{6}{2}(1 - q_3)q_3^2 \qquad (7)$$

$$\frac{V_{f2}}{a_3^3} = 1 - p_3^3 - \frac{6}{2}(1 - p_3)p_3^2 \qquad (8)$$

$$V_s = 1 - V_{f1} - V_{f2} \qquad (9)$$

The surface area of the interface between the first fluid phase and the solid phase of the structure 600, $A_{f1}$, is given by:

$$\frac{A_{f1}}{a_3^2} = \frac{24}{2}(1 - q_3)q_3 \qquad (10)$$

The surface area of the interface between the second fluid phase and the solid phase of the structure 600, $A_{f1}$, is given by:

$$\frac{A_{f2}}{a_3^2} = \frac{24}{2}(1 - p_3)p_3 \qquad (11)$$

As in the exemplary tilings 300, 400 discussed above with respect to FIGS. 3 and 4, respectively, as the unit cell edge length $a_3$ increases, the surface areas $A_{f1}$ and $A_{f2}$ increase in proportion to the square of the length $a_3$. Similarly, if smaller unit cells 500 are tiled in a given volume of the tiling 600, the surface areas in a given unit cell decrease but the overall surface areas in the given volume increase, because the number of unit cells in the volume increases in proportion to the cube of the length. Thus, the surface areas of the interfaces of each of the first and second fluid phases with the solid phase per unit volume of the tiling 600 is inversely proportional to a.

In some exemplary embodiments, the volumes of the first and second fluid phases in a structure are different. In other exemplary embodiments, the volumes of the first and second fluid phases in a structure are the same. It is readily determined that many different values of the parameters $p_3$ and $q_3$ will result in equal volume of the first and second fluid phases.

A face of a structure of tiled unit cells may be capped in various ways in order to constrain a fluid that is flowing within the structure. Referring now to FIGS. 7A-7D, a plurality of exemplary structures 700-706 are shown that incorporate a cap that facilitates constraining one or more fluids flowing in a structure of tiled unit cells. The structures 700-706 each comprise a 4×4×4 tiling of the unit cell 500 described above with respect to FIG. 5. Thus, similarly to the 3×3×3 tiling 600 of the unit cell 500, the structures 700-706 each define a first interior region and a separate second interior region, wherein first and second fluids flow in the first and second interior regions, respectively. For each of the three exemplary structures 700-706, three faces are shown.

Figures 7A, 7B:
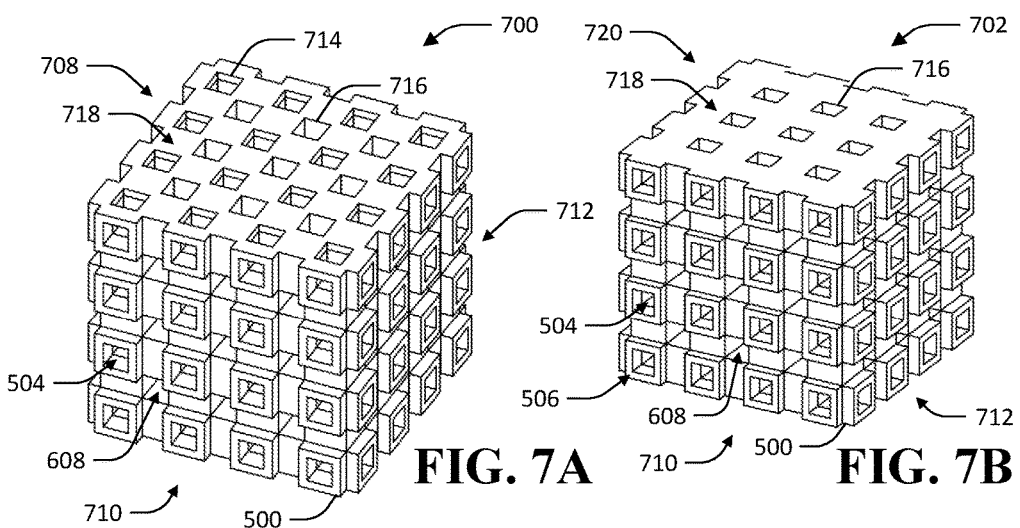
FIGS. 7A-7D are diagrams of an exemplary tiling of the unit cell of FIG. 5, illustrating caps for faces of the tiling.

Referring now solely to FIG. 7A, the exemplary structure 700 comprises a capped upper face 708 that provides access to both the first interior region and the second interior region of the structure 700, and two side faces 710, 712. The upper face 708 comprises a first set of openings 714 that provides access to a first interior region of the structure 700 (e.g., as accessed by way of openings 504 in faces 506 of unit cells 500 making up the side faces 710, 712). The upper face 708 further comprises a second set of openings 716 that provides access to a second interior region of the structure 700 (e.g., as accessed by way of voids 608 in the unit cells 500 making up side faces 710, 712). The upper face 708 comprises a flat surface 718 in which the openings 714, 716 are disposed. The flat surface 718 can facilitate mating of the structure 700 to other components, e.g., for the delivery of one or more fluids to the structure 700.

Figures 7C, 7D:
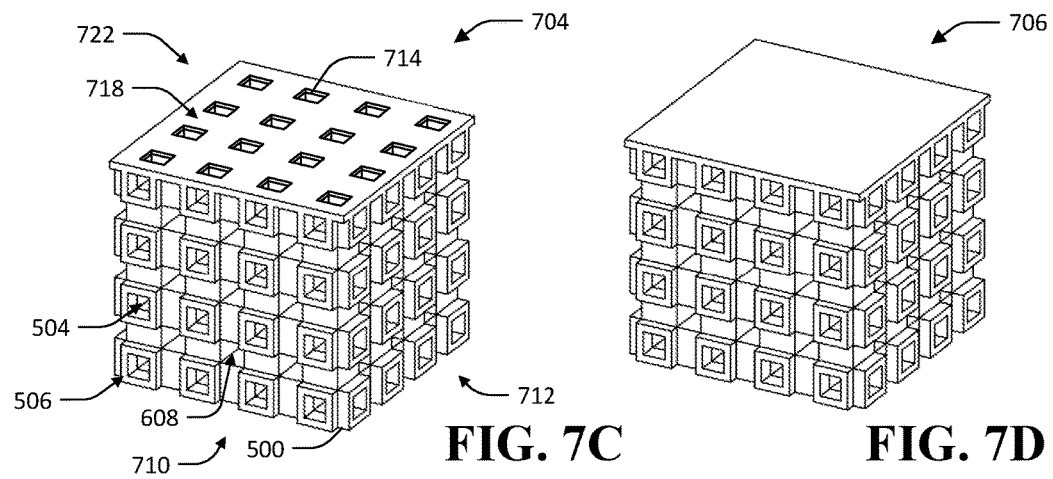

Referring now to FIG. 7B, the exemplary structure 702 comprises another exemplary capped upper face 720 that provides access solely to the second interior region of the structure 702 by way of openings 716. Referring now to FIG. 7C, the exemplary structure 704 comprises yet another exemplary capped upper face 722 that provides access solely to the first interior region of the structure 702 (e.g., as accessed by way of the openings 504 in the faces 506 of the unit cells 500) by way of openings 714. Referring now to FIG. 7D, the exemplary structure 706 comprises still yet another exemplary capped upper face 724 that consists of the flat surface 718. The capped upper face 724 does not provide access to either of the first or second interior regions of the structure 706, and may be used in circumstances where it is desirably to prevent inflow or outflow of fluid by way of a face of a structure. For example, in any of the exemplary structures 700-704, it may be desirable to provide input of fluid to the structures 700-704 at their respective upper faces 708, 720, 722 and constrain the fluid to flow out from the structures 700-704 solely by way of respective bottom faces (not shown) that are opposite the upper faces 708, 720, 722. In such example, four side faces (710, 712 and two remaining side faces not shown) of the structures 700-704 could be capped in similar fashion to the upper face 724 of the structure 706, thereby preventing outflow of fluid from the voids 608 or the openings 504 of the side faces of the unit cells 500.

Based upon the foregoing description, it is apparent that a structure for containing and directing flow of one or more fluids may be formed by tiling a unit cell to form a larger rectangular prism, providing inflow and outflow connections for the one or more fluid phases on opposite faces of the prism, and sealing the remaining four faces of the prism (e.g., as in the capped upper face 724 described above with respect to FIG. 7D). In some applications other configurations may be desirable.

In various embodiments, a structure for constraining and directing a fluid is formed by tiling unit cells within a volume for which the outer boundaries are aligned in a direction other than the x, y, and z directions that are aligned with a corner of the unit cell. For example, and referring now to FIGS. 8 and 9, structures 800 and 900 are illustrated wherein a unit cell with edge length a is first tiled l times in the x, y, and z directions extending from a corner of the unit cell along edges of the unit cell to fill a cube containing $l^3$ unit cells. The tiled structure is then cropped so that every point in the structure is on or between the central diagonal line that passes through points (0,0,0) and (a,a,a), and 6 planes that pass through an outer edge of a cube of length ma and are parallel to the central diagonal line, where m is a number of tilings of the unit cells that is smaller than l. In these exemplary structures, all flow paths within a unit cell form the same angle with respect to the diagonal, facilitating efficient transport of fluids through the structures. Furthermore, in the exemplary structures, flow paths of fluid within a unit cell form angles between zero and 90 degrees with respect to a direction of average direction of fluid flow through the structures, where the average direction of fluid flow extends in a direction from a fluid inlet of the structure to a fluid outlet of the structure (e.g., in a same direction as the central diagonal).

Figure 8:
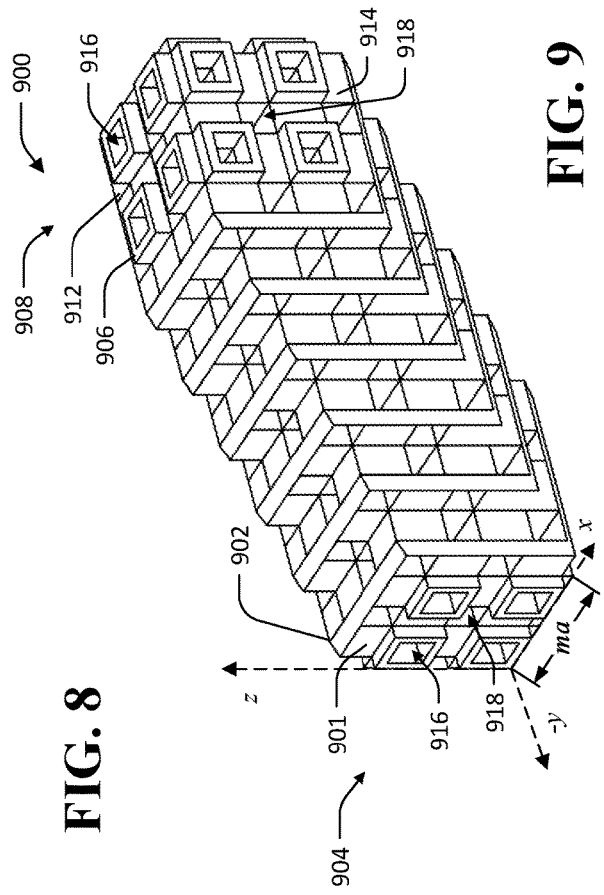
FIG. 8 is a diagram of another exemplary tiling of the unit cell of FIG. 2.

Referring solely now to FIG. 8, an exemplary structure 800 formed by tiling and cropping of unit cells is illustrated. The structure 800 is formed by a tiling of unit cells 200 described above with respect to FIG. 2. The value of m is 3, and l is 7.

Figure 9:
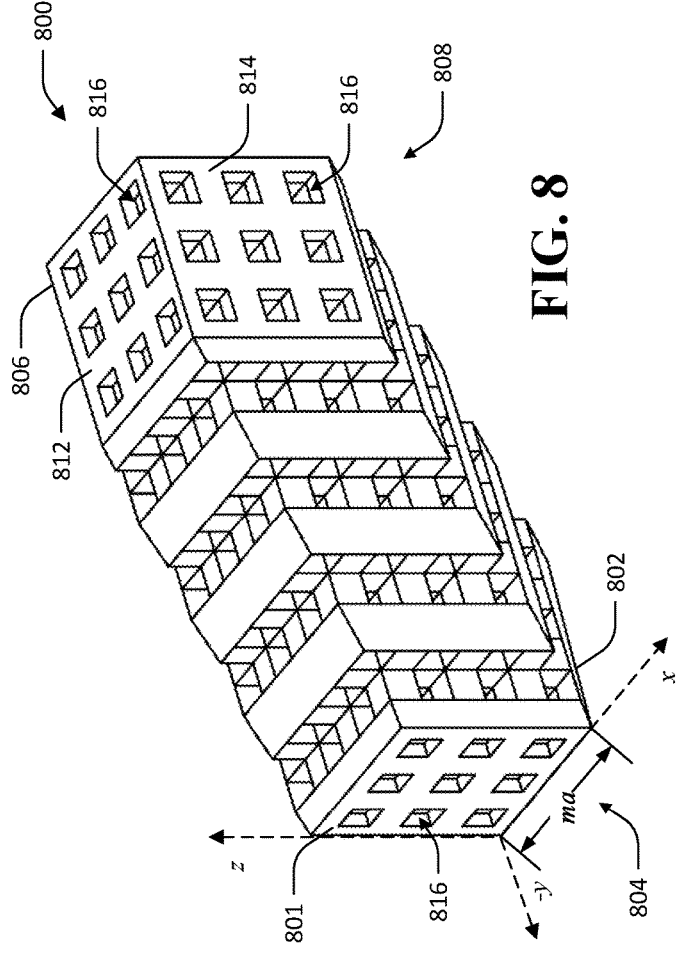
FIG. 9 is a diagram of another exemplary tiling of the unit cell of FIG. 5.

Referring solely now to FIG. 9, an exemplary bicontinuous structure 900 formed by tiling and cropping of unit cells is illustrated. The structure 900 is formed by a tiling of unit cells 500 described above with respect to FIG. 5. The value of m is 2, and l is 5.

Referring again to FIGS. 8 and 9, the corners of end faces of the structures 800 and 900 such as 810 and 910 can be categorized according to planes (not shown) that are perpendicular to a space diagonal direction that passes through corners (0,0,0) and (ma,ma,ma) of m×m×m cubes 802, 902. The coordinate system is defined as shown in FIGS. 8 and 9, wherein looking toward the origin (0,0,0) along the space diagonal, the axes z, y, and z appear in clockwise order. A plane is defined in the coordinate system as $$x+y+z=n \qquad (12)$$

where n is a constant. Table 1 shows the corners of a cube of edge length a aligned along the positive x, y, and z axes categorized according to their respective n planes, as well as the projection of each of these corners onto the n=0 and n=3a planes.

TABLE 1

| n | Corner x, y, z | n = 0a projection | n = 3a projection |
|---|---|---|---|
| 0a | 0, 0, 0 | 0, 0, 0 | a, a, a |
| 1a | 0, 0, a | (−1, −1, 2)a/3 | (2, 2, 5)a/3 |
|  | 0, a, 0 | (−1, 2, −1)a/3 | (2, 5, 2)a/3 |
|  | a, 0, 0 | (2,−1, −1)a/3 | (5, 2, 2)a/3 |
| 2a | 0, a, a | (−2, 1, 1)a/3 | (1, 4, 4)a/3 |
|  | a, 0, a | (1,−2, 1)a/3 | (4, 1, 4)a/3 |
|  | a, a, 0 | (1, 1, −2)a/3 | (4, 4, 1)a13 |
| 3a | a, a, a | 0, 0, 0 | a, a, a |

The projected points on each plane define the corners of a respective hexagon that has an edge length equal to $a\sqrt{2/3}$. A distance between opposite edges of the hexagon is $a\sqrt{2}$. The angle of the diagonal along which the unit cells 200, 500 are tiled in the structures 800, 900 versus the z axis is arccos $\sqrt{1/3}\approx54.73$ degrees while the angle of the diagonal versus its projection in the x-y plane is arccos $\sqrt{2/3}\approx35.26$ degrees.

An extension of the m×m×m tiling 802, 902 of the unit cells 200, 500 along the space diagonal can be defined by translating each of the corners of the cubes 802, 902 in the planes n=ma, 2ma, and 3ma and translating each of these corners by (1, 1, 1)ma. A number l-m of such extensions can be made, resulting in l of the unit cells 200, 500 disposed along a central axis of the respective structures 800, 900 that extends along the space diagonal. In the exemplary structures 800, 900, the extensions of the cubes 802, 902 are tiled with unit cells to completely fill the extended volume (including portions of unit cells along the boundary) and then truncated along a boundary of a hexagonal prism defined by projection of the 6 outer corners of the cubes 802, 902 onto planes n=0 and n=31a.

Each of the structures 800, 900 comprises two cubes, each of which makes up either of two ends of the structure. For example, referring now solely to FIG. 8, the structure 800 comprises the cube 802 at a first end 804 of the structure 800 and further comprises a second cube 806 at a second end 808 of the structure 800. The cubes 802 and 806 each comprise three faces, e.g., face 810 of unit cell 802 and faces 812, 814 of unit cell 806. Each of the faces 810-814 has openings 816 formed therein that serve as inlets and/or outlets for a fluid. The structure 800 defines an interior region for fluid flow by way of which the unit cells making up the structure 800 are connected. Fluid that enters the structure 800 by way of the openings 816 is constrained by the structure 800 to flow within the interior region until exiting the structure by way of one or more of the openings 816. For example, fluid entering the structure 800 by way of openings 816 at the second end 808 of the structure 800 may be constrained to exit the structure 800 by way of openings 816 at the first end 804 of the structure 800. A remainder of the volume bounded by external faces of the structure 800 that is not occupied by the fluid in the interior region is occupied by the solid fraction of the unit cells making up the structure 800.

Similarly, and referring now solely to FIG. 9, the structure 900 comprises the cube 902 at a first end 904 of the structure 900 and further comprises a second cube 906 at a second end 908 of the structure 900. The unit cells 902, 906 each comprise three faces, e.g., face 910 of cube 902 and faces 912, 914 of cube 906. Each of the faces 910-914 has openings 916 formed therein that serve as inlets and/or outlets for a first fluid. The faces 910-914 further have voids formed therein that serve as inlets and/or outlets for a second fluid. The structure 900 defines two separate interior regions for fluid flow by way of which the unit cells making up the structure 900 are connected. A first of the two interior regions is accessed by way of the openings 916 while a second of the two interior regions is accessed by way of the voids 918. A first fluid that enters the structure 900 by way of the openings 916 is constrained to flow within the first interior region and may only exit the structure 900 by way of another one of the openings 916. Likewise, a second fluid that enters the structure 900 by way of the voids 918 is constrained to flow within the second interior region and may only exit the structure 900 by way of another one of the voids 918. Similarly to the structure 800, a remainder of the volume bounded by external faces of the structure 900 that is not part of the first or second interior regions is occupied by the solid fraction of the unit cells making up the structure 900.

In some cases, the structures 800, 900 are formed by additive manufacturing methods such that one or more external faces of tiled unit cells that make up the structures 800, 900 (e.g., other than the outer faces of cubes 802, 806 and 902, 906) are intentionally not completely sealed. For example, it may be desirable to provide holes for removal of unconsolidated additive manufacturing material such as a powder or viscous liquid that might be difficult to remove solely through the openings 816 in the unit cells 802, 806 that make up the ends 804, 808 of the structure 800. Thus, it is to be understood that some portions of a structure may be added in a later manufacturing step to facilitate additive manufacturing of the structure.

In other exemplary embodiments, a tiling of unit cells is truncated to a desired shape or volume other than the hexagonal prism shape described above with respect to FIGS. 8 and 9. For example, a tiling of unit cells could be truncated to fit within a cylindrical shape, and unit cells of the tiling cropped along the boundary of the cylindrical shape accordingly. In another example, a tiling of unit cells could be cropped to fit within a rectangular prism. Other geometries are also contemplated.

Figure 10:
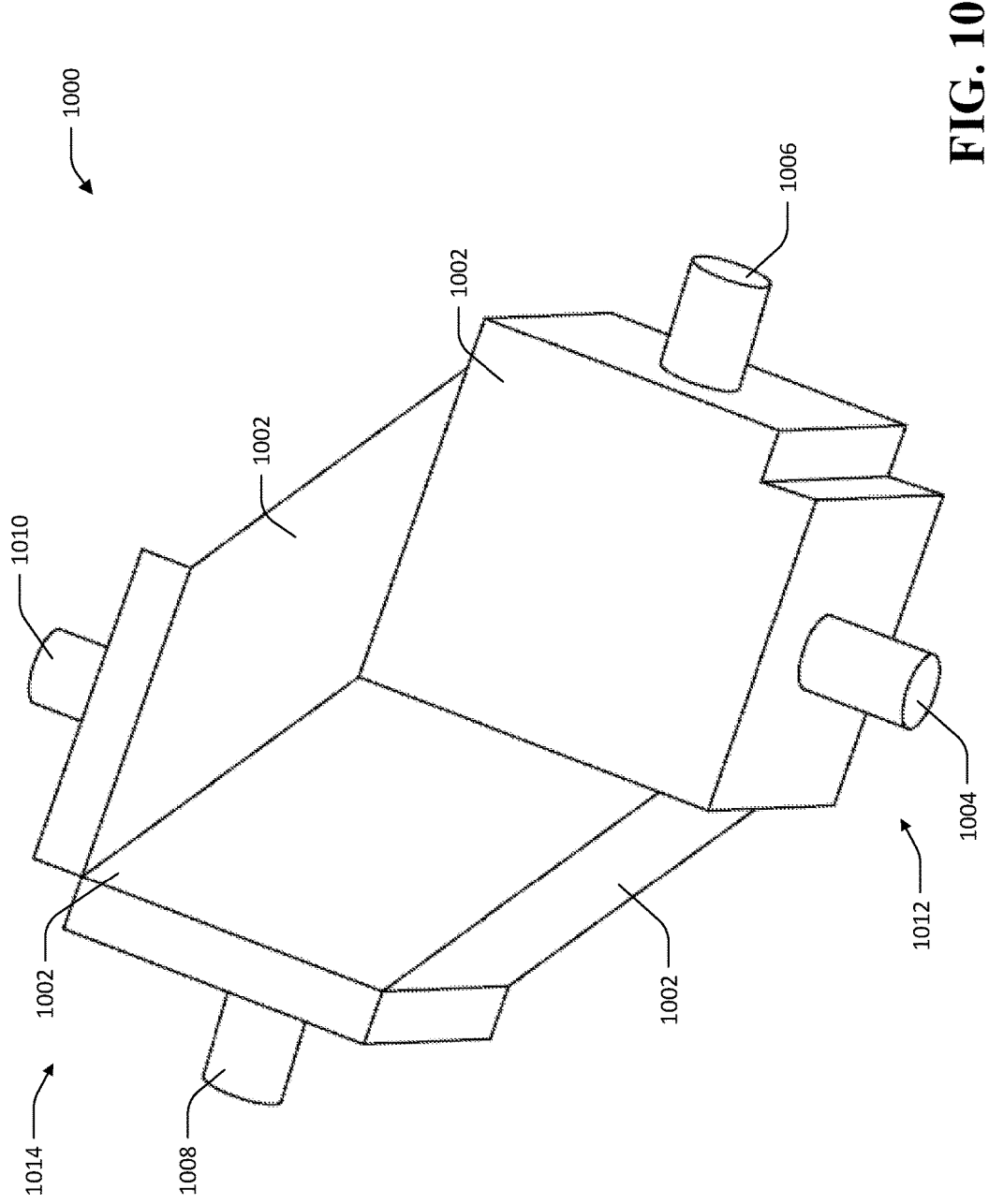
FIG. 10 is a diagram of an exemplary containment structure for directing fluid flow into and out of a structure of tiled unit cells.

Referring now to FIG. 10, an exemplary containment structure 1000 for containment of a monolithic structure of tiled unit cells (e.g., the structure 800 or the structure 900) is illustrated. The containment structure 1000 comprises a plurality of faces 1002 that together form an enclosed area within which the monolithic structure of tiled unit cells is contained. The containment structure 1000 further comprises four inlet/outlet ports 1004-1010, two ports 1004, 1006 at a first end 1012 of the structure 1000 and two ports 1008, 1010 at a second end 1014 of the structure 1000. In an exemplary embodiment, the containment structure 1000 may be configured for containment of a monolithic, bicontinuous structure of tiled unit cells that defines separate first and second interior regions of fluid flow. In the exemplary embodiment, the port 1004 can be configured as an inlet for a first fluid (e.g., by modifying an underlying face of the tiled structure, such as face 914 of structure 900, to correspond to the capping scheme of face 722 of FIG. 7C), the port 1006 can be configured as an inlet for a second fluid (e.g., by modifying the underlying face of the tiled structure, such as face 912 of the structure 900, to correspond to the capping scheme of face 720 of FIG. 7B), while the port 1008 can be configured as an outlet for the second fluid and the port 1010 can be configured as an outlet for the first fluid by appropriate modification of the underlying face of the tiled structure. The ports 1004-1010 are aligned with faces of the monolithic structure of tiled unit cells contained in the structure 1000. By way of example, if the structure 1000 contains the structure 900 depicted in FIG. 9, the ports 1004 and 1006 are aligned with faces 914 and 912 of the structure 900, respectively, which are each modified to provide selective access to only one fluid phase.

Figure 11:
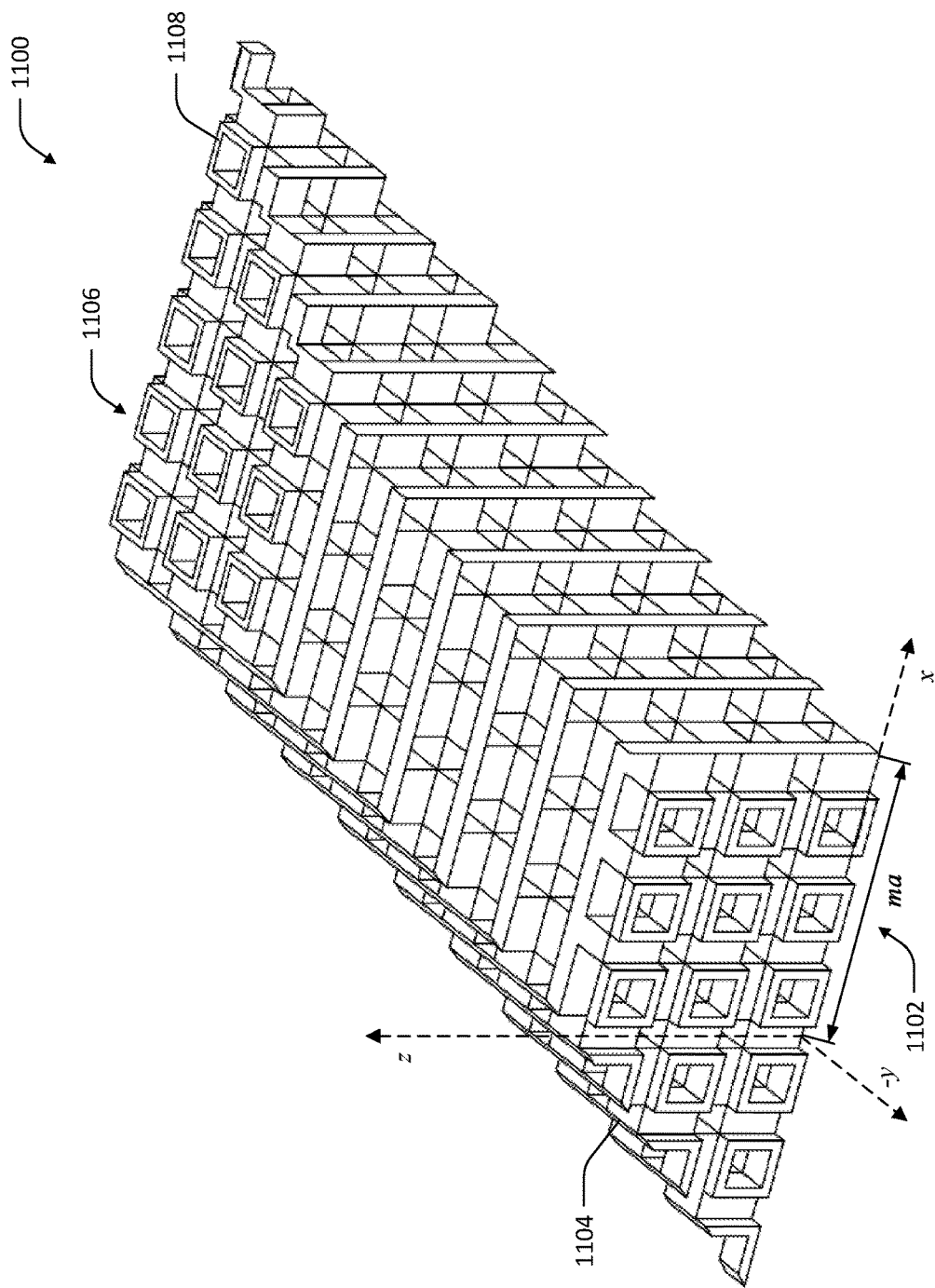
FIG. 11 is a diagram of still another exemplary tiling of the unit cell of FIG. 5 wherein the tiling is extended to form two end faces.

A tiled structure for containment and direction of a fluid may be extended along one or more faces in order to provide a flat face of greater area for interfacing with one or more inlet or outlet ports. Referring now to FIG. 11, an exemplary structure 1100 is illustrated, wherein the structure 1100 comprises a tiling of unit cells (e.g., the unit cells 500). As the structure 1100 is formed, the tiling is extended along a face 1102 of the tiling 1100, and the face parallel to the x-y plane not visible in FIG. 11, incorporating the face parallel to the y-z plane into the interior of the structure 1100, to form an extension 1104. The face 1102 of the tiling 1100 is extended by defining a new point by translating from a corner of the face parallel to the y-z plane that is farthest from the origin by (−ma,−ma,−ma) and extending the tiling 1100 of the unit cells to fill the extended volume, cropping or omitting unit cells that cross desired boundaries of the structure 1100. Thus, in the exemplary structure 1100 shown, the face defined by (0,0,0), (0,ma,0), (0,ma,ma), and (0,0,ma) is extended by translating the point (0,ma,ma) by (−ma,−ma,−ma) to yield the new point (−ma,0,0). A second face 1106, disposed at an opposite end of the structure 1100 from the first face 1102, is extended in a similar fashion to form extension 1108.

In other embodiments, it may be desirable to crop a tiled structure of unit cells to provide a single face at each end for delivery of fluid to the structure. Referring now to FIG. 12, a cut view of a portion of the end 808 of the structure 800 is shown wherein the end 808 has been cropped to provide a single face 1202. The end 808 of the structure 800 is cropped along a plane (not shown) that is perpendicular to the space diagonal along which the structure 800 is extended, as described in greater detail above with respect to FIG. 8. Intersection between the plane and the end of the structure defines different surface geometries of the face based upon the type of unit cells that are tiled to create the structure. Thus, in FIG. 12, the intersection of such a plane with the unit cells 200 making up the structure 800, when the plane is defined by Eq. 12 with integer values of n, defines a plurality of six-point star surfaces (e.g., 1204) disposed along the face 1202.

Referring now to FIG. 13, an exemplary containment structure 1300 that facilitates containment and delivery of fluid to of a tiled structure cropped to have a single face is illustrated. For example, the containment structure 1300 is suited to containment and delivery of fluid to the structure 800 modified to have a single flat face at each of the ends 804, 808 as described above with respect to FIG. 12. The structure 1300 comprises a hexagonal prism 1302 that has hexagonal faces (e.g., 1304) at each of two ends 1306, 1308 corresponding to ends 804, 808 of the structure 800, respectively, and six side panels (e.g., 1310-1314) extending between the hexagonal faces. The structure 1300 further comprises a fluid inlet port 1316, 1318 at each of the ends 1306, 1308, respectively. By way of example, an internal structure of the hexagonal face 1304, not shown in FIG. 13, is configured to receive fluid from the inlet port 1318 and to distribute the fluid across the face 1202 of the contained structure 800. The internal structure may contain modified unit cells, such as unit cells 200 with a doubled value of $a_2$, and halved value of $(1-q_2)$.

Figure 14:
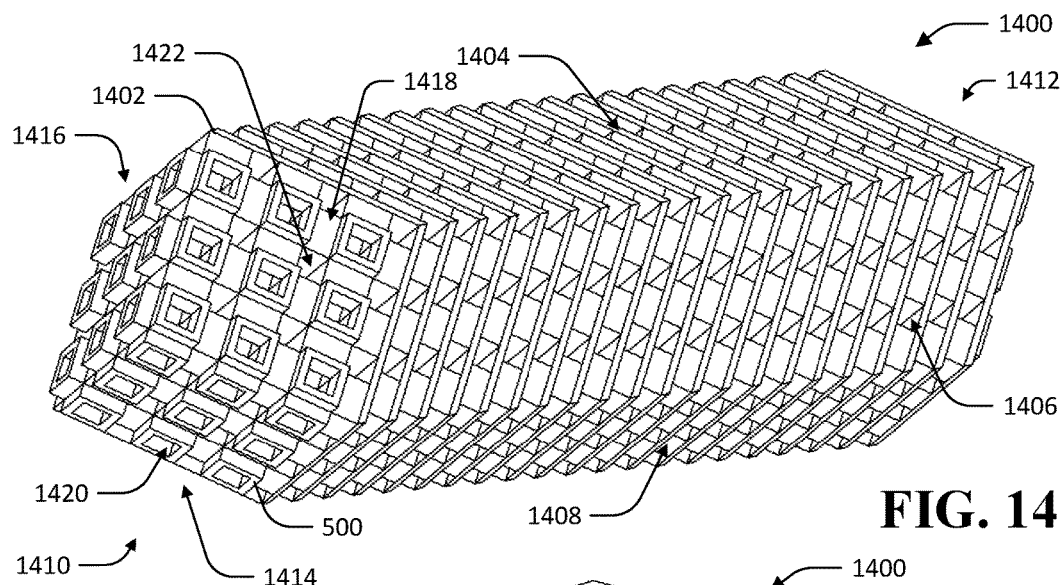
FIG. 14 is a diagram of an exemplary structure that facilitates directing separate flows of two different fluids.

Referring now to FIG. 14, a bicontinuous structure 1400 is illustrated. The structure 1400 comprises a tiling of the unit cells 500 extended along a diagonal in similar fashion to the structure 900 described above with respect to FIG. 9. For the structure 1400, m=3 and l=12. The structure 1400 is formed along boundaries of a hexagonal prism outer envelope (not shown), the structure 1400 having six side faces, e.g., 1404-1408. The structure 1400 has two ends 1410, 1412, each of the ends 1410, 1412 of the bicontinuous structure 1400 having three terminal faces (e.g., faces 1414-1418 of the end 1410) that serve as inlet/outlet ports of the structure 1400 where fluid may enter or exit separate first and second interior regions of the structure 1400. The first interior region of the structure 1400 is accessed by way of openings 1420 in faces of the unit cells 500, whereas the second interior region of the structure 1400 is accessed by way of voids 1422 between unit cells 500 defined by the arrangement of the cells 500 in the unit cell 1402.

In exemplary embodiments, the faces of the structure 1400 (e.g., 1414-1418) can be modified such that each face provides selective access to only one of the interior regions. For example, the face 1414 could be modified to provide selective access to the first interior region by capping the face 1414 as shown in FIG. 7C in order to block the voids 1422 and leave the openings 1420 clear. In another example, the face 1416 could be modified to provide selective access to the second interior region by capping the face 1416 as shown in FIG. 7B in order to block the openings 1420 and leave the voids 1422 clear. Further, the face 1418 could be modified to prevent access to either of the interior regions by capping the face 1418 as shown in FIG. 7D.

Figure 15A:
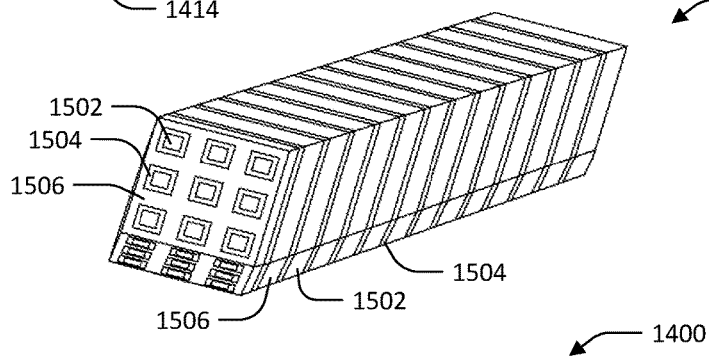
FIGS. 15A-15C are diagrams illustrating flows of fluids through first and second interior regions of the exemplary structure of FIG. 13.
Figure 15B:
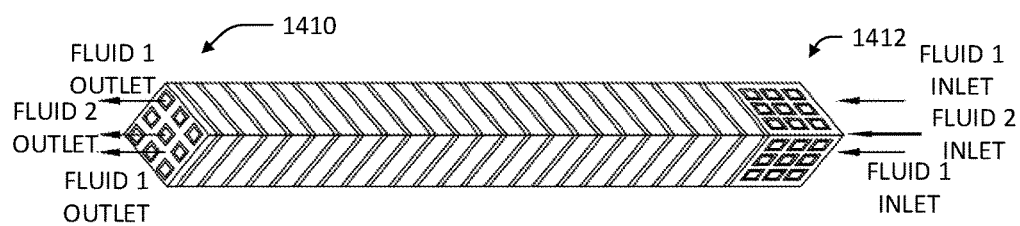
Figure 15C:
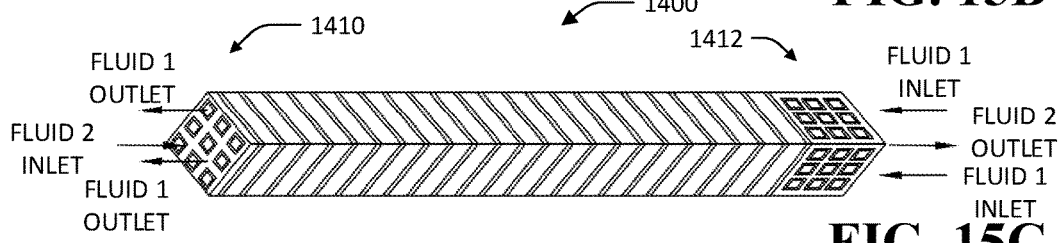

FIGS. 15A-C illustrate geometry of the solid phase of the structure 1300 as well as two fluid phases flowing in the first and second interior regions of the structure 1300. Referring now to FIG. 15A, locations of a first fluid phase 1502, a solid phase 1504 of the structure 1300, and a second fluid phase 1506 within the structure 1300 are shown. As the structure 1300 extends, the first fluid phase 1502 and the second fluid phase 1506 alternate in bands beneath the exterior face of the structure 1300, separated by bands of the solid phase 1504 of the structure 1300 itself.

In an exemplary application of the structure 1300 as a heat exchanger, the heat exchanger can be operated in co-current or counter-current modes. Referring now to FIG. 3B, the co-current mode of operation is illustrated wherein the two fluid phases enter the structure 1300 at the end 1312 and exit the structure 1300 at the end 1310. On a given end face, only one fluid enters or exits. At end 1310, fluid 2 exits from the face that is shown, and fluid 1 exits from the two faces behind it. At end 1312, fluid 1 enters the two faces that are shown, and fluid 2 enters the face that is behind them. Referring now to FIG. 15C, the counter-current mode of operation is illustrated wherein the first fluid phase enters the structure 1300 at the end 1312 of the structure and exits the structure 1300 at the opposite end 1310, while the second fluid phase enters the structure 1300 at the end 1310 and exits the structure 1300 at the opposite end 1312. At end 1310, fluid 2 enters the face that is shown, and fluid 1 exits from the two faces behind it. At end 1312, fluid 1 enters from the two faces that are shown, and fluid 2 exits from the face that is behind them. The counter-current mode of operation of the structure 1300 is well-suited to use of the structure 1300 as a heat exchanger.

Figure 16:
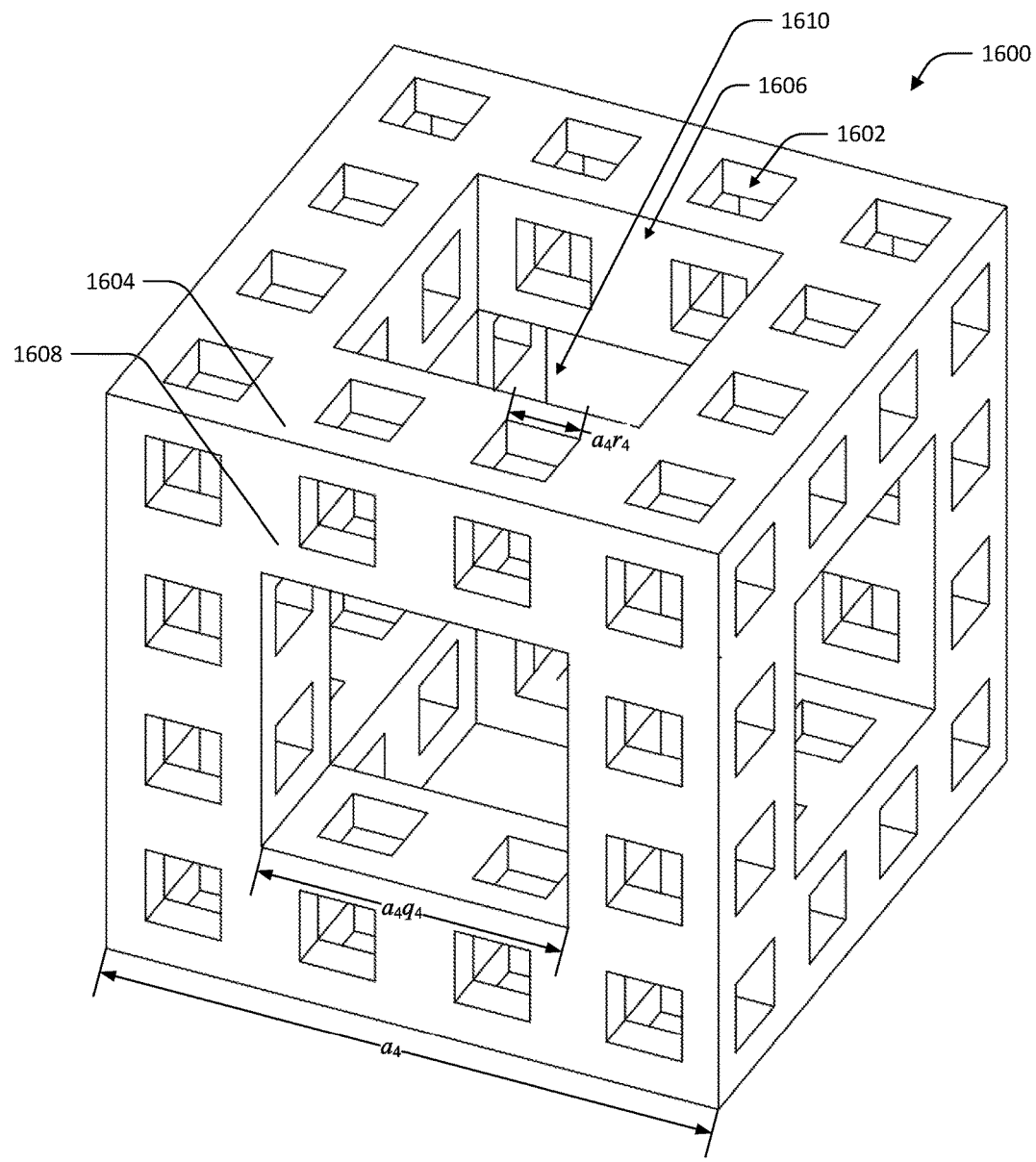
FIG. 16 is a diagram of an exemplary unit cell wherein pores are formed to improve fluid-solid contact in the unit cell.

FIG. 16 illustrates an exemplary unit cell 1600 wherein the unit cell 1600 has a plurality of pores 1602 disposed therein to increase fluid-solid contact in the unit cell 1600. The unit cell 1600 is a cubic-edge unit cell similar to the unit cell 200. The unit cell 1600 comprises struts 1604 that are disposed along edges of a cube of length $a_4$. The unit cell 1600 comprises square openings 1606 of length $q_4 a_4$ in its faces 1608. The length of the square pores 1602, $r_4 a_4$, is defined separately from the length of the openings 1606. The pores 1602 are each smaller in volume than an interior region 1610 of fluid flow through the unit cell 1600 that is defined by the openings 1606. The pores 1602 increase surface area of the boundary between solid and fluid phases of the unit cell 1600 as compared to the unit cell 200 and aid in fluid flow through the unit cell 1600.

In other exemplary embodiments it is to be understood that a tiling may be a successive tiling wherein a first unit cell is tiled a plurality of times to define a second unit cell, which is subsequently tiled to form a structure, or a third unit cell. For example, any of the exemplary cells 100, 200, 500 may be tiled a plurality of times to define respective second unit cells (e.g., the structures 300, 400, 600, and 1600, respectively). The second unit cells may then be tiled a plurality of times to create other, more complex structures. More complex structures created with either the first or second unit cells may branch, turn corners, provide inlets at locations other than the ends, and/or provide outlets at locations other than the ends.

Figure 17:
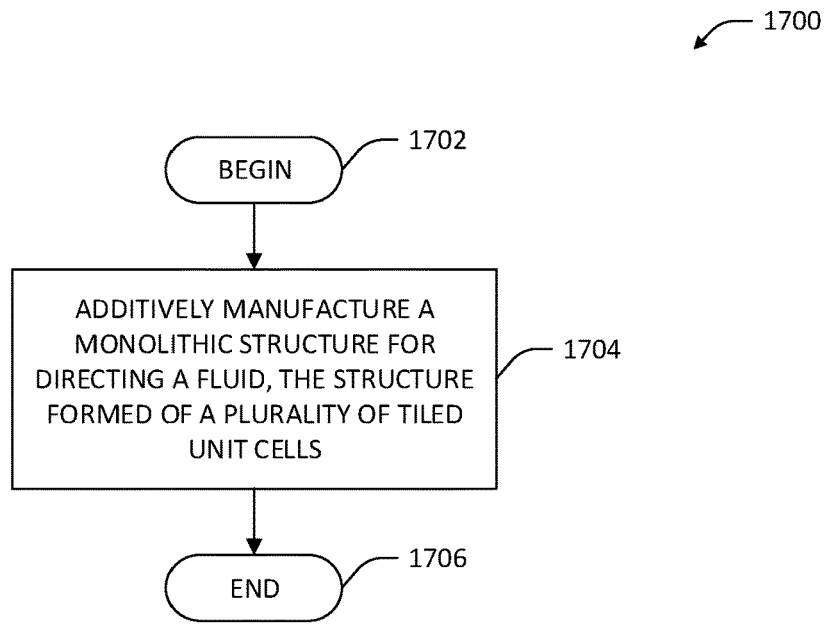
FIG. 17 is a flow diagram that illustrates an exemplary methodology for forming a monolithic structure of tiled unit cells for containing and directing flow of a fluid.

FIG. 17 illustrates an exemplary methodology relating to manufacture of integrated structures for containing and directing flow of a fluid. While the methodology is shown and described as being a series of acts that are performed in a sequence, it is to be understood and appreciated that the methodology is not limited by the order of the sequence. For example, some acts can occur in a different order than what is described herein. In addition, an act can occur concurrently with another act. Further, in some instances, not all acts may be required to implement a methodology described herein.

Referring now to FIG. 17, a methodology 1700 that facilitates additive manufacturing of a monolithic structure for direction and containment of a flow of a fluid is illustrated. The methodology 1700 begins at 1702, and at 1704 a monolithic structure for directing a fluid is additively manufactured. The monolithic structure is additively manufactured such that the structure is formed of a plurality of tiled unit cells. In an embodiment, the structure is manufactured so that the unit cells are arranged to define an interior region of fluid flow, an inlet to the interior region of fluid flow, and an outlet from the interior region of fluid flow. The unit cells are tiled so that an average direction of fluid flow is in a diagonal direction extending from a first corner of a first unit cell to a second corner of the first unit cell, the second corner being opposite the first corner. In an exemplary embodiment, the average direction of fluid flow extends between the inlet and the outlet. In further embodiments, the structure is manufactured so that the unit cells are arranged to define a second interior region of fluid flow separate from the first interior region, a second inlet to the second interior region, and a second outlet from the second interior region. First and second fluids flow in the first and second regions such that the fluids flow through the unit cells in directions at an angle to the average direction of fluid flow, where the angle is between zero and 90 degrees. The monolithic structure is formed by additive manufacturing methods such that the plurality of unit cells are integrated as a single component rather than being constructed with discrete components. In other embodiments, the entirety of the structure is formed as a single component with substantially no physical separation between parts of the structure. In exemplary embodiments, the monolithic structure is additively manufactured by methods such as projection stereolithography, multiphoton lithography, fused filament fabrication, laser sintering, etc. The methodology 1700 completes at 1706.

What has been described above includes examples of one or more embodiments. It is, of course, not possible to describe every conceivable modification and alteration of the above devices or methodologies for purposes of describing the aforementioned aspects, but one of ordinary skill in the art can recognize that many further modifications and permutations of various aspects are possible. Accordingly, the described aspects are intended to embrace all such alterations, modifications, and variations that fall within the spirit and scope of the appended claims. Furthermore, to the extent that the term "includes" is used in either the details description or the claims, such term is intended to be inclusive in a manner similar to the term "comprising" as "comprising" is interpreted when employed as a transitional word in a claim.

What is claimed is:

1. An apparatus for directing flow of a fluid, comprising: a plurality of tiled unit cells, the unit cells arranged so that a fluid flows through the unit cells at an angle to an average direction of the fluid's flow through the apparatus, the angle being greater than zero and less than 90 degrees, the unit cells arranged to define a volume comprising:
   a first region in which the fluid flows through the unit cells; and
   a second region occupied by solid portions of the unit cells, wherein fluid is impeded from flowing in the second region, wherein the volume is entirely occupied by the first and second regions, and wherein the solid portions of each of the unit cells have a plurality of pores formed therein, the pores configured to improve fluid-solid contact in the apparatus.

2. The apparatus of claim 1, wherein each unit cell comprises a three-dimensional (3D) cross, the 3D cross comprising a solid central cube, wherein a respective strut extends from each of six faces of the solid central cube.

3. The apparatus of claim 1, wherein each unit cell is a cube having a hollow interior portion, wherein each face of the cube comprises an opening to the hollow interior portion.

4. The apparatus of claim 1, wherein a first unit cell in the unit cells comprises a plurality of second unit cells, the second unit cells arranged to form the first unit cell, the second unit cells having a same shape.

5. The apparatus of claim 1, wherein the plurality of tiled unit cells are formed as a monolithic structure.

6. The apparatus of claim 1, wherein each unit cell is a hexagonal prism.

7. A device for containing and directing flows of fluids, comprising:
   a plurality of tiled unit cells, wherein each of the unit cells comprises a three-dimensional cross, the three-dimensional cross comprising:
   a solid cubic shell having a hollow interior portion, and
   six struts, each of the six struts extending from a respective face of the cubic shell, each of the six struts having a respective face, and wherein the faces of each of the six struts have respective openings formed therein, wherein an opening of a strut in the six struts extends through the strut to the hollow interior portion of the cubic shell, the unit cells arranged to define:
   a first interior region of fluid flow; and
   a second interior region of fluid flow, the second interior region separate from the first interior region such that a first fluid in the first region does not mix with a second fluid in the second region, wherein the unit cells are tiled so that the first fluid flows through the unit cells at a first angle to an average direction of flow of the first fluid through the device and the second fluid flows through the unit cells at a second angle to the average direction of flow of the second fluid through the device, the first and second angles between zero and 90 degrees.

8. The device of claim 7, a first unit cell in the unit cells comprising a plurality of second unit cells, the plurality of second unit cells arranged to form the first unit cell, the second unit cells having a same shape.

9. The device of claim 7, wherein the plurality of tiled unit cells are at least partially enclosed by a hexagonal prism.

10. The device of claim 7, further comprising:
    a first inlet to the first interior region;
    a second inlet to the second interior region;
    a first outlet from the first interior region; and
    a second outlet from the second interior region.

11. The device of claim 10, wherein the first and second outlets and first and second inlets are positioned such that the average direction of flow of the first fluid is different from the average direction of flow of the second fluid.

12. The device of claim 10, wherein the first and second outlets and first and second inlets are positioned such that the average direction of flow of the first fluid is the same as the average direction of flow of the second fluid.

13. The device of claim 7, wherein the device is formed as a monolithic structure.

14. The device of claim 7, wherein the plurality of unit cells have a same shape.

15. The device of claim 7, the unit cells arranged to further define:
    a first face, the first face configured to access the first interior region and not the second interior region; and a second face, the second face configured to access the second interior region and not the first interior region.

16. The device of claim 7, further comprising a plurality of exterior surfaces, the exterior surfaces arranged to constrain a fluid flow to within the first and second interior regions of fluid flow.

17. A method, comprising:

additively manufacturing a monolithic structure for containing and directing flows of first and second fluids, wherein the structure is formed of a plurality of tiled unit cells wherein each of the unit cells comprises a three-dimensional cross, the three-dimensional cross comprising: a solid cubic shell having a hollow interior portion; and six struts, each of the struts extending from a respective face of the cubic shell, each of the struts having a respective face, and wherein the faces of each of the struts have respective openings formed therein, wherein the openings extend through the struts to the hollow interior portion of the cubic shell, the unit cells arranged to define a first interior region of fluid flow, a first inlet to the first interior region of fluid flow, a first outlet from the first interior region of fluid flow, a second interior region of fluid flow, a second inlet to the second interior region of fluid flow, and a second outlet from the second interior region of fluid flow, wherein the unit cells are tiled so that the first fluid flows in the first interior region of fluid flow at an angle between zero and 90 degrees relative to a first direction extending from the first inlet to the first outlet, and the second fluid flows through the second interior region of fluid flow at an angle between zero and 90 degrees relative to a second direction extending from the second inlet to the second outlet.

18. The method of claim 17, wherein additively manufacturing the structure comprises manufacturing the structure by at least one of multiphoton lithography, fused filament fabrication, laser sintering, or projection stereolithography.

* * * * *